(12) United States Patent
Davis

(10) Patent No.: US 6,866,043 B1
(45) Date of Patent: Mar. 15, 2005

(54) AMBULATORY THERAPEUTIC FOOTWEAR

(76) Inventor: William Davis, 100 W. Main, P.O. Box 324, Utica, MN (US) 55979

( * ) Notice: Subject to any disclaimer, the term of this patent is extended or adjusted under 35 U.S.C. 154(b) by 306 days.

(21) Appl. No.: 10/133,294

(22) Filed: Apr. 26, 2002

(51) Int. Cl.⁷ .................................................. A61F 6/02
(52) U.S. Cl. ......................... 128/842; 128/882; 602/27; 602/28
(58) Field of Search ............................ 602/23, 28, 29, 602/36, 27, 60, 62, 63, 65, 66; 128/842, 882; 2/22, 911, 919; 36/1, 1.5, 140, 83; D2/911, 909; D24/192

(56) References Cited

U.S. PATENT DOCUMENTS

| | | | |
|---|---|---|---|
| 5,056,509 A | * 10/1991 | Swearington ................. | 602/29 |
| D323,239 S | 1/1992 | Rooke | |
| D326,556 S | 6/1992 | Rooke | |
| 5,282,483 A | * 2/1994 | Wang .......................... | 128/882 |
| 5,501,659 A | * 3/1996 | Morris et al. .................. | 602/27 |
| 5,582,579 A | * 12/1996 | Chism et al. .................. | 602/36 |
| 6,022,332 A | * 2/2000 | Nelson ......................... | 602/27 |
| 6,361,514 B1 | * 3/2002 | Brown et al. .................. | 602/23 |
| 6,602,215 B1 | * 8/2003 | Richie, Jr. ..................... | 602/27 |
| 6,689,081 B2 | * 2/2004 | Bowman ...................... | 602/27 |

* cited by examiner

*Primary Examiner*—Fadi H. Dahbour
(74) *Attorney, Agent, or Firm*—DL Tschida

(57) ABSTRACT

A cloth covered, thermally insulated therapeutic boot. Hook and loop fasteners and straps are arrayed about the boot to control the support angle between the foot and calf. Numerous other hook and loop fasteners are fitted to the boot surfaces to secure panels that wrap to define the boot. A contour shaped and vented foam calf support is secured to the boot to support the calf and elevate the heel within the boot, when the boot is supported. Hinge pieces mount between the calf support and a rigid heel cradle. Hook and loop fasteners secure the hinge straps to the calf support. Compressible, flanged hinge pins mount to the hinge straps to permit rotations relative to stops.

34 Claims, 5 Drawing Sheets

AMBULATORY THERAPEUTIC FOOTWEAR

BACKGROUND OF THE INVENTION

The present invention relates to therapeutic footwear and, in particular, to an insulated, fleece-lined, cloth boot having a hinged heelpiece, polyurethane calf support and several hook and loop fastened straps and wrappings that retain the calf support to the boot and the boot to the foot.

A variety of leg wear and footwear have been developed for pre and post-operative patient therapy situations. These items are worn to prevent vasoconstriction and promote vasodilation to maintain blood circulation and thereby prevent clotting. They also physically protect and warm the legs and feet from skin trauma such as ulcerations, cracking and abrasions. By keeping the legs and feet warm, the blood vessels don't constrict and the blood flow is maintained.

Applicant sells fleece-lined footwear of the foregoing type. A fleece-lined, hook and loop fastened boot is shown in U.S. Pat. Des. 326,556.

Other manufacturers sell footwear to accommodate the foregoing and other conditions. Such footwear can include features to prevent foot drop. Extraneous braces are also available for use with the footwear to permit walking.

The present improved footwear was developed to provide therapeutic footwear that intrinsically prevents foot drop, permits ambulation and significantly off-loads weight from the heel. Weight is particularly shifted from the heel to the posterior surface of the calf via a raised conformal contour. The boot is constructed with a fleece lining to insulate the foot and calf. A semi-rigid, ventilated foam insert having a contoured interior surface supports the calf when lying in a reclined position. The heel is simultaneously elevated and displaced away from contact with the footwear and particularly an adjacent heel cradle. The rigid heel cradle includes a hinged hook and loop strap piece that mates with a fastener attached to the foam support. Numerous other hook and loop fasteners are fitted to the cloth surfaces and attach to straps and cover pieces that wrap to secure the calf support and heel cradle to the boot and configure the boot about the foot. An anti-rotation bar is fastens beneath a heel cover piece to prevent abduction/obduction.

SUMMARY OF THE INVENTION

It is accordingly a primary object of the invention to provide thermally insulated footwear for pre and post-operative recuperation to stimulate blood circulation.

It is a further object of the invention to provide a fleece lined fabric boot with a number of hook and loop fasteners fitted to the boot surfaces, depending straps and cover pieces that collectively wrap and attach together to configure the boot.

It is a further object of the invention to provide a fleece lined fabric boot with a ventilated foam insert that supports the calf when lying in a reclined position.

It is a further object of the invention to provide a ventilated foam insert having a conformal contoured interior surface that supports the calf and elevates the heel away from a heel cradle (i.e. off-loads weight from the heel), when lying in a reclined position.

It is a further object of the invention to provide a fleece lined fabric boot with a rigid heel cradle that includes a hinged hook and loop strap piece that mates with a fastener attached to the foam support.

It is a further object of the invention to provide a flexible hinge pin means to detachably secure a hinged hook and loop strap piece to a rigid heel cradle and rotation limiting means to control foot movement during ambulation.

The foregoing objects, advantages and distinctions of the invention are obtained in a presently preferred fleece lined, fabric boot of the invention. The boot has several tabs of hook and loop fastener materials arrayed about the boot that mate with associated straps and cover pieces. The straps and cover pieces align to define and control the fitting of the boot. Detachable straps also extend from the upper surfaces of the boot to the toe region to prevent foot drop.

A concave polyurethane foam calf support mounts within the boot. Ventilation apertures are formed in the calf support. The longitudinal interior surface of the support presents a raised, contoured surface that conforms to the calf and elevates the heel when weight is shifted onto the back of the calf support. The calf support is contained between the fabric cover and insulated liner. Hook and loop fasteners secured to overlapping flaps of the boot cover are aligned along the posterior longitudinal surface of the cover to secure the support to the boot.

A rigid heel cup or cradle includes hinged hook and loop strap pieces that mate with fasteners attached to the foam support. Split, compressible, flanged hinge pins project from the heel cup and cooperate with rotation-limiting slots and captured pins to control movement of the heel cup relative to the calf support. Transverse hook and loop fasteners attached to the heel cup and a fabric cover piece that covers the heel and sole regions contain the heel/sole cover to the heel cup to the boot. The foam support and heel cup can thereby rotate relative to one another to permit ambulation.

Still other objects, advantages, distinctions and constructions of the invention will become more apparent from the following description with respect to the appended drawings. Similar components and assemblies are referred to in the various drawings with similar alphanumeric reference characters. The description should not be literally construed in limitation of the invention. Rather, the invention should be interpreted within the broad scope of the further appended claims.

Figure 1:
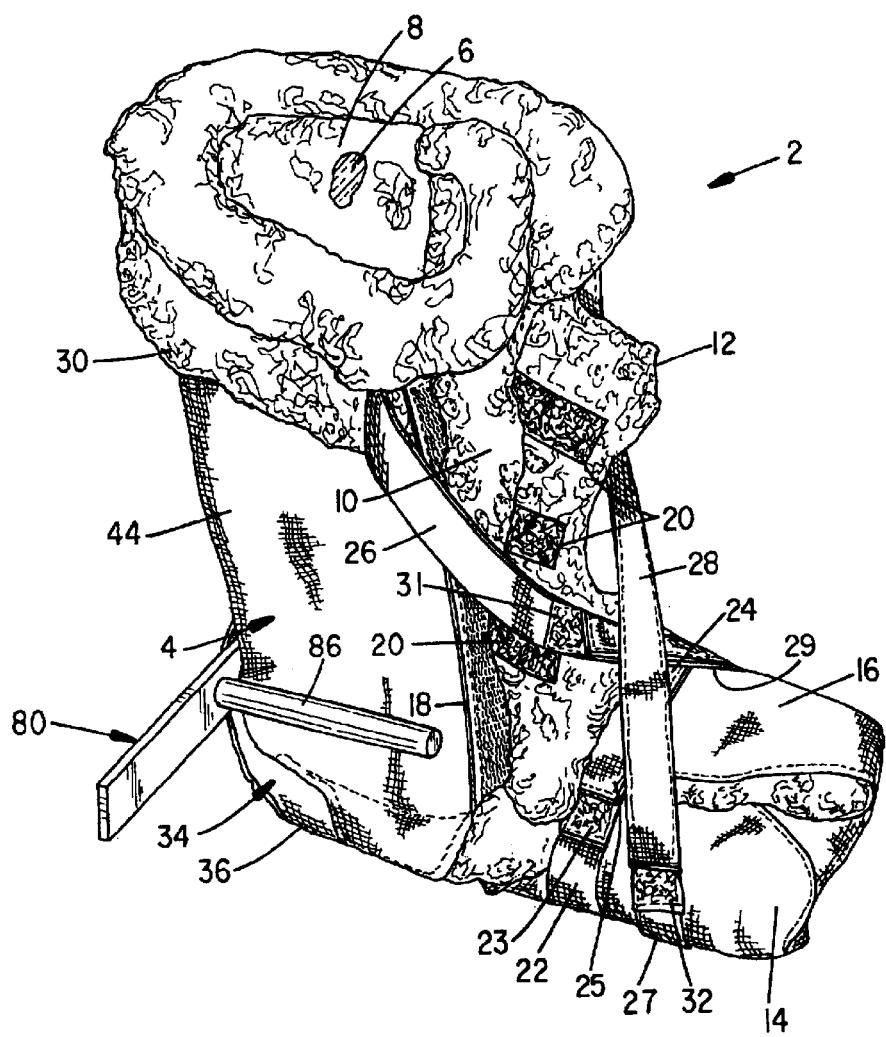
FIG. 1 is a perspective drawing of the boot with the boot strapped closed and an abduction bar shown at FIG. 5 secured thereto.

Similar structure throughout the drawings is referred to with the same alphanumeric reference numerals and/or characters.

DESCRIPTION OF THE PREFERRED EMBODIMENT

Figure 2:
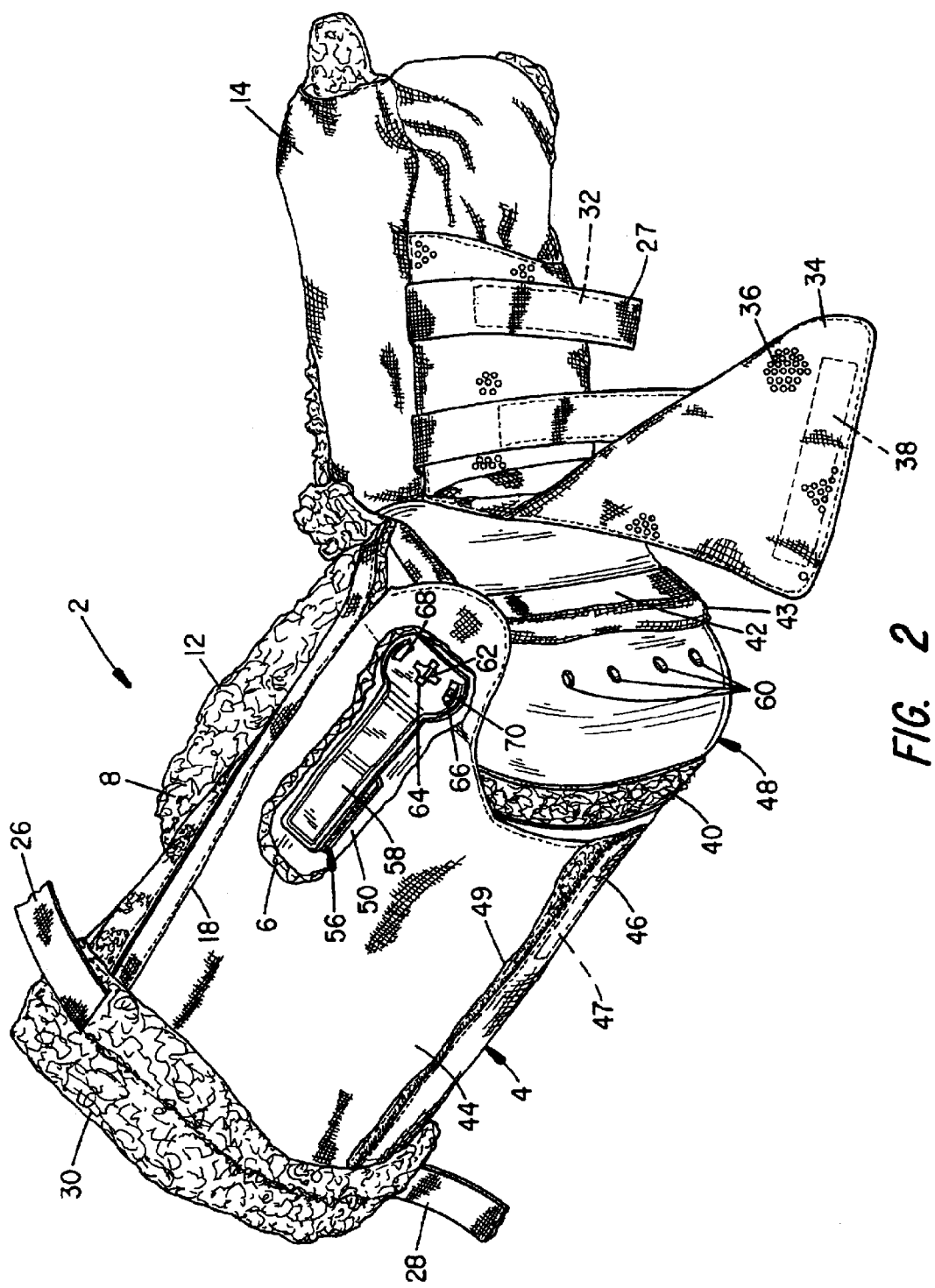
FIG. 2 is a perspective drawing shown in partial cutaway and showing the boot folded open and exposing a foam calf support and hinged heel cradle.

Referring to FIGS. 1 and 2, perspective views are shown to the improved therapeutic boot 2 of the invention. The boot 2 is covered with an air permeable outer fabric cover 4. The cover 4 is sewn from a durable velour cloth. Other materials such as a heavyweight cotton or cordura, among other fabrics, can also be used. A thermal insulation liner 6 (shown in cutaway), such as THINSULATE, can be sewn or attached to the cover 4 or beneath a separate lining. The interior surface of the boot 2 and/or lining 6 is faced with a fleece lining 8. The lining 8 provides a soft comfortable surface that contacts the skin. The fleece 8 traps air, yet permits air circulation around the foot and leg to enhance the thermal insulation properties of the boot 2.

The boot 2 opens full-length along its front or anterior surface at right and left front or tongue panels 10 and 12 and right and left foot panels 14 and 16. The panels 10–16 wrap and overlap each other. Strips of hook and loop fasteners 18 and 20 are aligned along the longitudinal edge of the front panel 10 and in spaced, transverse relation along the interior of the front panel 12. Separate straps 22 and 24 are fitted with strips of hook and loop fastener material 23 and 25 and mount over the foot panels 14 and 16. When the panels 14 and 16 are overlapped, the straps 22 and 24 bind the foot and toes in the boot 2.

Straps 26 and 28 extend from a portion of a fleece collar 30 of the boot 2 and contain hook and loop tabs 31. Another set of straps 27 and 29 that contain mating hook and loop tabs 32 extend from the lateral sides of the toe panels 14 and 16. Upon securing the straps 26, 29 and 27,28 together, the angle between the foot and calf is fixed. In normal circumstances, the angle is set to prevent over-extension of the foot in either a reclined or walking posture.

With additional attention to FIG. 2, a heel and sole panel 34 is sewn to the toe panels 14 and 16 in the region of the sole of the boot 2. The panel 34 is covered with beads of nylon tufting 36 to provide traction, although exterior of the panel 34 could be plain. The tufting 36 or any other traction enhancing material can be applied to the panel 34 in any desired manner or pattern to facilitate traction. The posterior or heel end of the panel 34 includes a transverse strip 38 of hook and loop material that mates with a strip 40 secured to a rigid heel cup or cradle 48. The boot 2 is thereby able to freely rotate at the heel cup 48 and the panel 34 is free to flex during ambulation. More details to this attachment and the effected possible ambulation are discussed below.

The panel 34 also covers an elastic strap or panel 42 that extends between leg panels 44 and 46 that align with the calf. The panel 42 extends across the bottom of the heel cup 48 and over a foam pad 43 that covers the interior and a portion of the bottom surface of the rigid heel cup 48. The panels 34 and 42 retain the heel cup 48 and a rigid foam, channel piece or calf support 50 to the boot 2. Overlapping edges of the leg panels 44 and 46 are separately secured together along the posterior surface of the calf support 50 with mating longitudinal strips 47 and 49 of hook and loop fastener material.

The calf support 50 is contained in a pocket formed between the cover 4 and lining 8 along the lengths of the leg panels 44 and 46. The detachable strips 47 and 49 facilitate the mounting of the support 50 to the boot 2.

Figure 3:
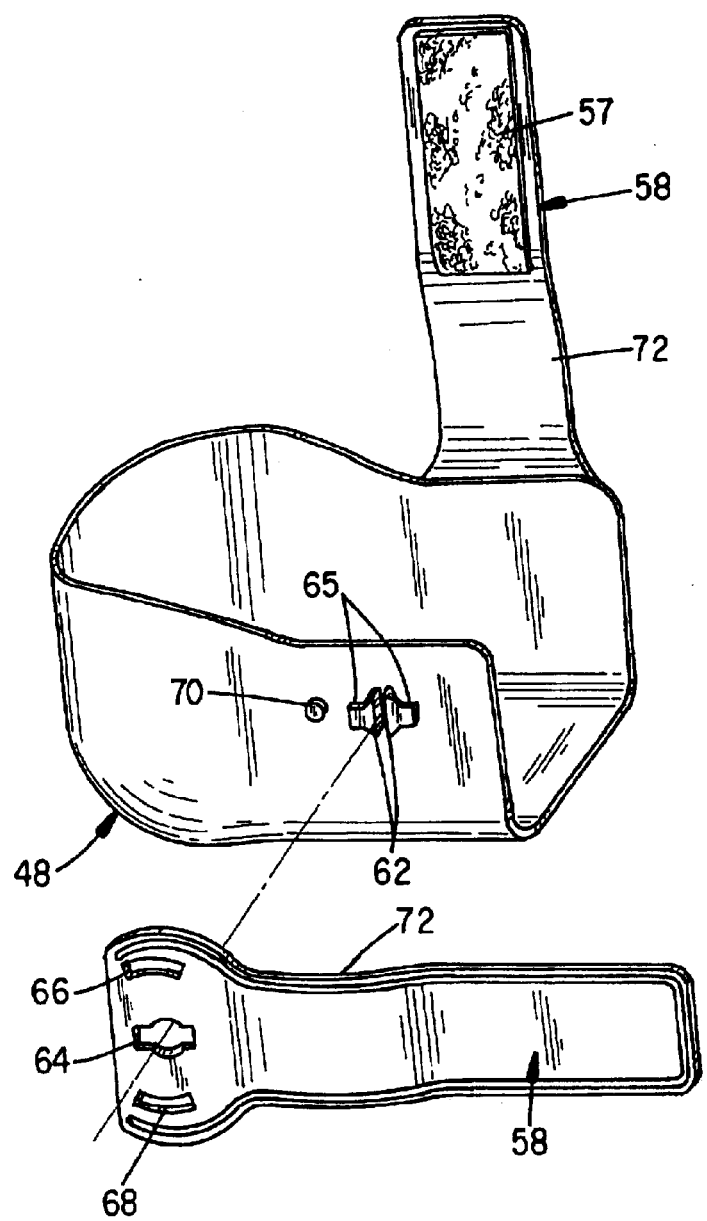
FIG. 3 is a perspective drawing shown in exploded assembly and showing the heel cup or cradle and ambulatory hinge.
Figure 4:
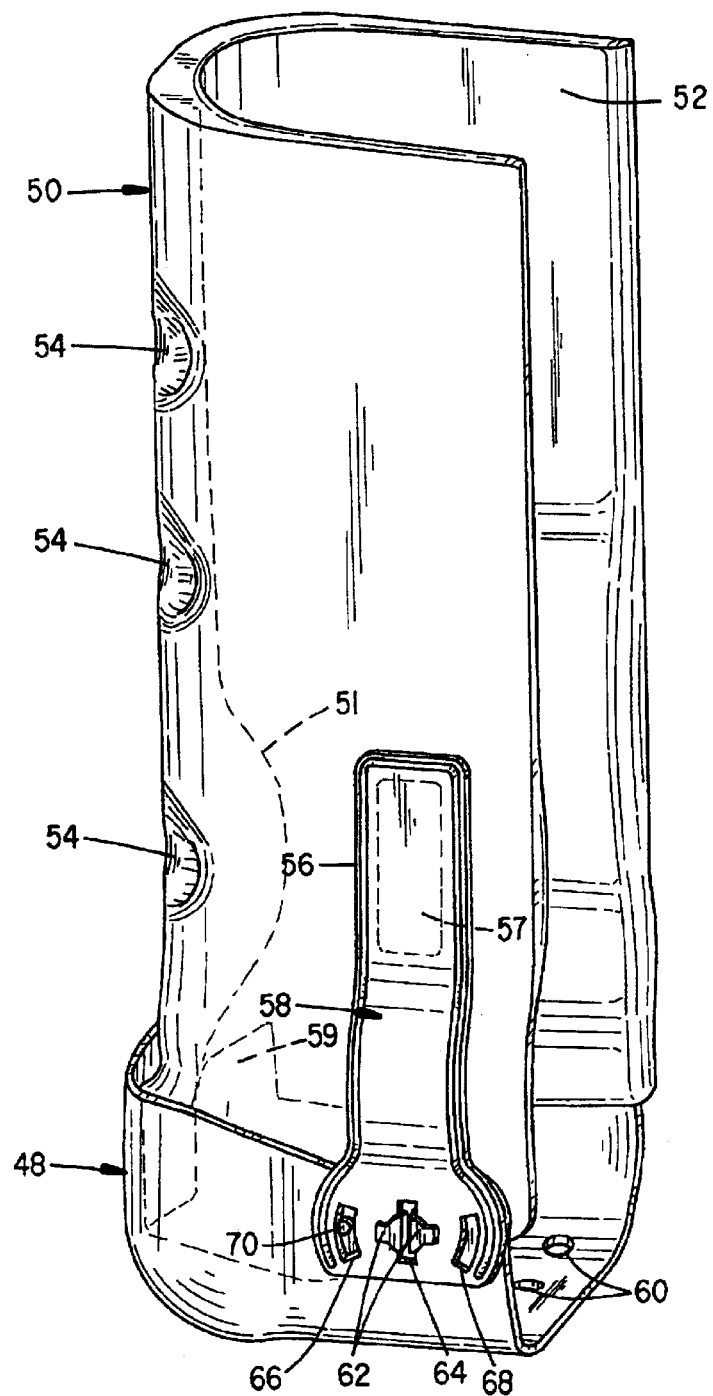
FIG. 4 is a perspective drawing showing the calf support mounted to the heel cradle.

With additional attention to FIGS. 3 and 4, details are shown to the heel cup 48 and calf support 50. The calf support 50 is molded from polyurethane foam, although a variety of foams and semi-rigid plastics can be used. The foam is selected to exhibit a sufficient durometer to compress and conform to the calf yet support the calf such that the heel only minimally contacts the heel cup 48.

The calf support 50 is formed with an open-ended, longitudinal channel or trough 52 that contains the calf. The wall thickness of the calf support 50 is profiled to be thicker at the posterior surface and taper inward as the walls extend around the calf to the edges adjacent the front panels 10 and 12. A raised, contoured surface or bump 51 is aligned in the region of the Achilles tendon to assure the heel doesn't contact the heel cup 48 and/or is supported in non-load bearing relation thereto. A number of vent holes 54 extend through the support 50 along the posterior surface of the support 50 to facilitate airflow when the leg is supported for protracted periods. Strips of hook and loop fastener material 56 are also affixed to the exterior sides of the calf support 50 and mate with tabs 57 at the hinge straps 58 that extend from the heel cup 48.

The heel cup 48 is constructed from a rigid nylon or plastic material and includes a number of vent holes 60. The cup 48 extends vertically to a region beneath the ankle. The cup 48 provides a rigid interface that shrouds and protects the posterior and bottom surfaces of the heel. The cup 48 is particularly shaped and sized to assure minimal contact with the heel when the leg is supported and limit contact with the heel and ankle during walking to prevent abrasion.

The calf support 50 extends into and cushions the sides and rear of the cup 48, except in the region of a "U-shaped" cutout 59. The pad 43 cushions the bottom interior of the cup 48. Collectively, the lower edges of the support 50 and pad 43 comfortably support and protect the heel when the user elects to walk on the boot 2.

Walking is facilitated via the novel manner of attaching the calf support 50 to the heel cup 48. In particular, the hinge straps 58 that extend from the tabs 57 at the calf support 50 mount to the sides of the heel cup 48 and interlock with flexible hinge pins 62 that align with a keyed, hinge slot 64 in each strap 58. Flanges or bent locking tabs 65 at the ends of the pins 62 detachably secure the straps 58 to the heel cup 48. One or both of two adjacent slots 66 and 68 align with a limit or stop member 70 that projects from the cradle 48. The rotation of each hinge strap 58 is limited by the cooperation of the stop 70 and slots 66 and/or 68.

The hinge straps 58 are molded from a flexible nylon and although relatively rigid, provide a degree of flexion. An outwardly extending, curved or bowed section 72 is formed in the region of the ankle. Upon properly fitting the hinge strap 58 to the calf support 50 and the boot 2 to a user, the heel cup 48 can rotate without contacting the ankle and the fleece lining 8, support 50 and cushion pad 43 protect the ankle.

Figure 5:
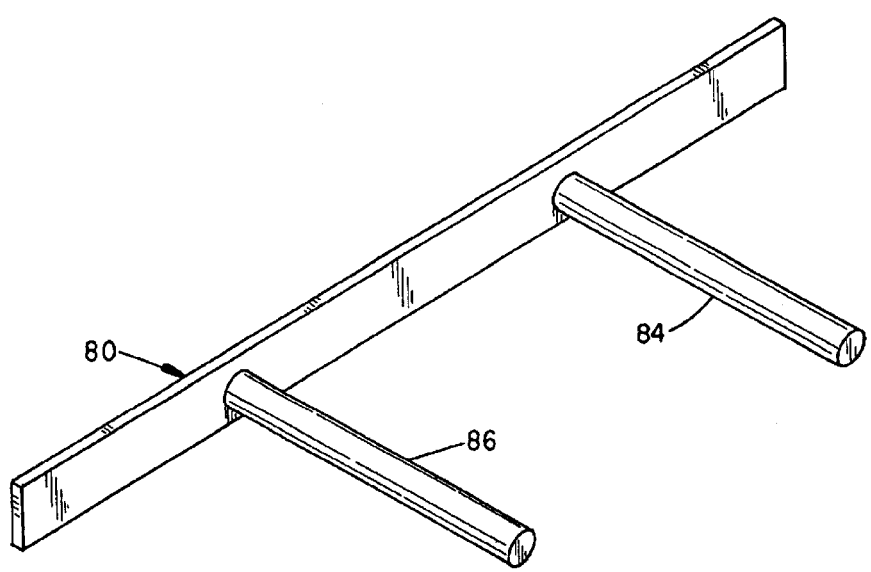
FIG. 5 is a perspective drawing showing an abduction bar that mounts to the boot in the region of the juncture between the calf support and heel cup to prevent rotation of the boot.

FIG. 5 depicts an abduction bar 80 that can be mounted to the boot 2 in the region of the juncture between the calf support 50 and heel cup 48, such as shown in FIG. 1. The bar 80 includes a horizontal section 82 and vertical risers 84 and 86. The foot is secured to the bar 80 in the region between the risers 84 and 86. The bar 80 is secured beneath the panel 34 in the region of the fasteners 38 and 40. The length of the bar 80 and risers 84 and 86 are sized to prevent rotation and generally restrict movement of the boot 2 and foot.

The boot 2 advantageously protects and thermally insulates the foot and lower leg of pre and post-operative users. The cooperation of the calf support 50 and hinged heel cup 48 permits ambulation without the extraneous supports. The heel cup 48 and calf support 50 can also be removed and detached from one another to facilitate cleaning or repair.

While the invention has been described with respect to a number of preferred constructions and considered improvements or alternatives thereto, still other constructions may be suggested to those skilled in the art. It is to be appreciated that selected ones of the foregoing features can be used singularly or be arranged in different combinations to provide a variety of improved footwear. The foregoing description should therefore be construed to include all those embodiments within the spirit and scope of the following claims.

What is claimed is:

1. Therapeutic footwear apparatus comprising:
   a) a boot comprising a plurality of fabric panels sewn to one another and organized to wrap about and cover a portion of the leg and foot and including a plurality of fasteners secured to said panels and wherein said fasteners are arranged to secure the wrapped boot to the leg and foot;
   b) a channel piece mounted to said boot and having a longitudinal cavity shaped to contain a portion of the leg; and
   c) a cup piece mounted to said channel piece and having a cavity shaped to mount about the heel, wherein said channel and cup pieces are hinged together, and wherein said plurality of panels cover said channel and cup pieces.

2. Footwear apparatus as set forth in claim 1 wherein said plurality of fasteners comprise a plurality of tabs of hook and loop fastener material mounted to said fabric panels and arranged to fasten over the top of the foot and front of the calf.

3. Footwear apparatus as set forth in claim 1 wherein said fabric panels are lined with a fleece material.

4. Footwear apparatus as set forth in claim 1 wherein a portion of a sole panel overlaps and fastens to said cup piece and such that said cup piece can rotate independent of adjoining leg panels that cover the calf.

5. Footwear apparatus as set forth in claim 4 wherein portions of first and second leg panels along a posterior surface of the channel piece overlap and fasten together to retain said channel piece between said leg panels and a liner secured to said plurality of panels, whereby detachment of said sole panel and said overlapping leg panels permits the insertion and extraction of said channel and cup pieces.

6. Footwear apparatus as set forth in claim 1 including a member mounted to said cup piece and projecting transverse to the foot to prevent rotation of the foot when supported in a reclined position.

7. Footwear apparatus as set forth in claim 1 including a stop member for limiting the rotation of said channel piece relative to said cup piece.

8. Footwear apparatus as set forth in claim 7 wherein first and second straps depend from said channel piece and wherein first and second axles respectively project from said cup piece into a bore of said first and second straps to define first and second hinge connections between said channel and cup pieces.

9. Footwear apparatus as set forth in claim 8 wherein said first and second axles each comprise a plurality of displaced flexible members and wherein each flexible member includes an axle surface upon which said first and second straps rotate and a flanged portion that extends transverse to said axle surface, whereby said plurality of flexible members compress to permit mounting of said first and second straps to said cup and expand to retain said first and second straps thereto.

10. Footwear apparatus as set forth in claim 8 wherein said first and second straps are fastened to said channel piece with tabs of hook and loop fastener material.

11. Footwear apparatus as set forth in claim 8 wherein a stop member projects from said cup piece into the path of rotation of one of said first and second straps to limit the relative rotation of said cup piece and said channel piece.

12. Footwear apparatus as set forth in claim 8 including a stop member mounted to project from said cup piece into a slot at one of said first and second straps for limiting the rotation of said cup piece relative to said channel piece.

13. Footwear apparatus as set forth in claim 1 wherein said channel piece is constructed of a rigid foam and includes a plurality of vent apertures and a raised surface that projects in the region of the Achilles tendon, such that when the leg is supported in a reclined position the calf is supported by said raised surface and the heel is held in a non-load bearing condition away from said cup piece.

14. Footwear apparatus as set forth in claim 1 including first and second length adjustable straps that extend from a collar region to a foot region of said boot to fix the relative angle between the foot and leg.

15. Footwear apparatus as set forth in claim 1 wherein said plurality of panels define an open ended pocket that contains the channel piece and wherein a retainer secures said cup and channel pieces to said boot.

16. Footwear apparatus as set forth in claim 15 wherein said retainer comprises an elastic strap.

17. Footwear apparatus as set forth in claim 15 wherein said pocket includes first and second leg panels along the channel piece that overlap and fasten together to retain said channel piece between said first and second leg panels and a liner secured to said first and second leg panels.

18. Footwear apparatus as set forth in claim 15 wherein a portion of a sole panel overlaps and fastens to said cup piece and such that said cup piece can rotate independent of adjoining leg panels that cover the calf.

19. Footwear apparatus as set forth in claim 1 wherein first and second straps are secured to said channel piece with hook and loop fastener material and wherein said first and second straps are hinge coupled to said cup piece.

20. Footwear apparatus as set forth in claim 1 wherein said channel piece comprises a foam material and wherein said cup piece comprises a plastic material.

21. Therapeutic footwear apparatus comprising:
   a) a boot comprising a plurality of fabric panels lined with a fleece material and sewn to one another and organized to wrap about and cover a portion of the leg and foot and including a plurality of hook and loop fasteners secured to said panels and arranged to secure the wrapped boot to the leg and foot;
   b) a foam channel piece mounted to said boot and having a longitudinal cavity shaped to contain the calf and including a plurality of apertures and a raised surface adjoining the Achilles tendon; and
   c) a cup piece mounted to said channel piece and having a cavity shaped to mount about the heel and wherein said plurality of panels cover said channel and cup pieces.

22. Footwear apparatus as set forth in claim 21 wherein said channel and cup pieces are hinged together.

23. Footwear apparatus as set forth in claim 21 wherein first and second straps that each contain a bore depend from said channel piece, wherein first and second axles project from said cup piece into the respective bores of said first and second straps to define first and second hinge connections between said channel and cup pieces and including a stop member that projects from said cup piece to limit the rotation of said cup piece relative to said channel piece.

24. Footwear apparatus as set forth in claim 23 wherein said first and second axles each comprise a plurality of displaced flexible members, wherein each flexible member includes an axle surface upon which one of said first and second straps rotates and a flanged portion that extends transverse to said axle surface, whereby said plurality of flexible members compress to permit mounting of said first and second axles to said first and second straps and expand to retain said first and second straps thereto.

25. Therapeutic leg and footwear apparatus comprising:
 a) a boot comprising a plurality of fleece lined fabric panels sewn to one another and organized to wrap about and cover portions of the leg and foot and including a plurality of hook and loop fasteners secured to said panels and arranged to secure the wrapped boot to the leg and foot;
 b) a foam channel piece mounted to said boot and having a longitudinal cavity shaped to mount about the calf and including a plurality of vent holes and a raised surface aligned to contact the Achilles tendon; and
 c) a cup piece secured to said channel piece for relative rotation and having a cavity shaped to mount about the heel, wherein portions of first and second leg panels along the channel piece overlap and fasten together to retain said channel piece to said boot and wherein a portion of a sole panel overlaps and fastens to said cup piece and such that said cup piece can rotate independent of said first and second leg panels, whereby detachment of said sole panel and said first and second leg panels permits the insertion and extraction of said channel and cup pieces from said boot.

26. Footwear apparatus as set forth in claim 25 wherein first and second straps depend from said channel piece, wherein first and second axles project between said first and second straps and said cup piece to define first and second hinge connections between said channel piece and said cup piece, and wherein a plurality of stop members project between said cup piece and each of said first and second straps.

27. Footwear apparatus as set forth in claim 25 wherein first and second axles hinge couple said channel piece to said cup piece, and wherein said first and second axles each comprise a plurality of displaced flexible members, whereby said plurality of flexible members compress to permit mounting said cup piece to said channel piece and expand to retain said cup piece to said channel piece.

28. Footwear apparatus as set forth in claim 25 including first and second length adjustable straps that extend from a collar region of said boot to a foot region to fix the relative angle between the foot and leg.

29. Therapeutic footwear apparatus comprising:
 a) a boot comprising a plurality of fabric panels sewn to one another and organized to cover a portion of the leg and foot and including a plurality of fasteners secured to said panels and wherein said fasteners are arranged to secure the boot to the leg and foot;
 b) a channel piece mounted to said boot and having a longitudinal cavity shaped to contain a portion of the leg; and
 c) a cup piece mounted to rotate relative to said channel piece and having a cavity shaped to mount about the heel, wherein said plurality of panels cover said channel and cup pieces, and wherein a portion of a sole panel overlaps and fastens to a posterior surface of said cup piece and such that said cup piece can rotate independent of adjoining leg panels that cover the calf.

30. Therapeutic footwear apparatus comprising:
 a) a boot comprising a plurality of fabric panels sewn to one another and organized to wrap about and cover a portion of the leg and foot and including a plurality of fasteners secured to said panels and wherein said fasteners are arranged to secure the wrapped boot to the leg and foot;
 b) a foam channel piece mounted to said boot and having a longitudinal cavity shaped to contain the calf and Achilles tendon; and
 c) a cup piece hinged to said channel piece and having a cavity shaped to mount about the heel and wherein said plurality of panels cover said channel and cup pieces.

31. Therapeutic footwear apparatus comprising:
 a) a boot comprising a plurality of fabric panels sewn to one another and organized to cover a portion of the leg and foot and including a plurality of fasteners secured to said panels and wherein said fasteners are arranged to secure the boot to the leg and foot;
 b) a channel piece mounted to said boot and having a longitudinal cavity shaped to contain a portion of the leg and wherein said channel piece is constructed of a rigid foam and includes a plurality of vent apertures and a raised surface that projects in the region of the Achilles tendon; and
 c) a cup piece mounted to said channel piece and having a cavity shaped to mount about the heel, wherein said plurality of panels cover said channel and cup pieces, and wherein when the leg is supported in a reclined position the calf is supported by said raised surface and the heel is held in a non-load bearing condition away from said cup piece.

32. Therapeutic footwear apparatus comprising:
 a) a boot comprising a plurality of fabric panels sewn to one another and organized to wrap about and cover a portion of the leg and foot and including a plurality of fasteners secured to said panels and wherein said fasteners are arranged to secure the wrapped boot to the leg and foot;
 b) a channel piece mounted to said boot and having a longitudinal cavity shaped to contain a portion of the leg;
 c) a cup piece mounted to said channel piece and having a cavity shaped to mount about the heel and wherein said plurality of panels cover said channel and cup pieces; and
 d) first and second length adjustable straps that extend from a collar region to a foot region of said boot to fix the relative angle between the foot and leg.

33. Therapeutic footwear apparatus comprising:
 a) a boot comprising a plurality of fabric panels sewn to one another and organized to cover the leg and foot and including a plurality of fasteners secured to said panels and wherein said fasteners are arranged to secure the boot to the leg and foot;
 b) a channel piece mounted within an open ended pocket of said boot and having a longitudinal cavity shaped to contain a portion of the leg; and
 c) a cup piece secured to said boot and mounted to rotate relative to said channel piece and having a cavity shaped to mount about the heel.

34. Therapeutic footwear apparatus comprising:
 a) a boot comprising a plurality of fabric panels sewn to one another and organized to define an open-ended pocket and wrap about and cover a portion of the leg and foot and including a plurality of fasteners secured to said panels and wherein said fasteners are arranged to secure the wrapped boot to the leg and foot;
 b) a channel piece mounted in said pocket and having a longitudinal cavity shaped to contain a portion of the leg; and
 c) a cup piece hinge coupled to said channel piece and having a cavity shaped to mount about the heel, and wherein said plurality of panels cover said channel and cup pieces.

* * * * *